(12) United States Patent
Nakagawa et al.

(10) Patent No.: US 9,977,846 B2
(45) Date of Patent: May 22, 2018

(54) PRODUCT QUALITY CONTROL METHOD

(75) Inventors: Hiroshi Nakagawa, Kanagawa (JP); Makoto Kamada, Kanagawa (JP); Jin Maeda, Kanagawa (JP)

(73) Assignee: Daiichi Sankyo Company, Limited, Chuo-ku (JP)

( * ) Notice: Subject to any disclaimer, the term of this patent is extended or adjusted under 35 U.S.C. 154(b) by 881 days.

(21) Appl. No.: 14/129,858

(22) PCT Filed: Jul. 6, 2012

(86) PCT No.: PCT/JP2012/067287
§ 371 (c)(1),
(2), (4) Date: Jan. 2, 2014

(87) PCT Pub. No.: WO2013/008733
PCT Pub. Date: Jan. 17, 2013

(65) Prior Publication Data
US 2014/0136157 A1    May 15, 2014

(30) Foreign Application Priority Data

Jul. 8, 2011   (JP) .................. 2011-152194

(51) Int. Cl.
*G06F 17/50* (2006.01)
*A61K 31/444* (2006.01)
(Continued)

(52) U.S. Cl.
CPC ........ *G06F 17/5009* (2013.01); *A61K 31/444* (2013.01); *G05B 15/02* (2013.01);
(Continued)

(58) Field of Classification Search
CPC ..... G06F 17/5009; G05B 15/02; G05B 17/02; A61K 31/444; A61K 9/2853; A61J 3/005; G01N 33/15
(Continued)

(56) References Cited

U.S. PATENT DOCUMENTS 7,379,783 B2   5/2008   Popp
7,379,784 B2   5/2008   Popp
(Continued)

OTHER PUBLICATIONS

"Application Form for Sakura Tablet: Mock-Up for the Manufacture Method, Specifications, and Test Method Columns of Drug Product (Sample Description)," Application for Sakura tablet _V2_01_0900310 for translation, n.d., <http://www.nihs.go.jp/drug/section3/English%20mock%20App.pdf>, 13 pages.
(Continued)

*Primary Examiner* — Saif A Alhija
(74) *Attorney, Agent, or Firm* — Christensen O'Connor Johnson Kindness PLLC

(57) ABSTRACT

A real-time release testing capable of constantly ensuring quality, a method for quality testing of a product using real-time release testing, a method for quality testing of an in-process product and/or an end product by real-time release testing, comprising the step of assessing the quality from design space established with only material attributes as inputs, and a manufacturing parameter-independent method for quality testing of a product using real-time release testing.

13 Claims, 7 Drawing Sheets

(51) Int. Cl.
  G05B 15/02 (2006.01)
  G05B 17/02 (2006.01)
  A61J 3/00 (2006.01)
  G01N 33/15 (2006.01)
  A61K 9/28 (2006.01)

(52) U.S. Cl.
  CPC .............. G05B 17/02 (2013.01); *A61J 3/005* (2013.01); *A61K 9/2853* (2013.01); *G01N 33/15* (2013.01)

(58) Field of Classification Search
  USPC .......................................................... 703/1
  See application file for complete search history.

(56) References Cited

U.S. PATENT DOCUMENTS

| | | |
|---|---|---|
| 7,392,107 B2 | 6/2008 | Popp |
| 7,428,442 B2 | 9/2008 | Popp |
| 7,444,197 B2 | 10/2008 | Popp |
| 7,471,991 B2 | 12/2008 | Popp |
| 7,509,185 B2 | 3/2009 | Popp |
| 7,799,273 B2 | 9/2010 | Popp |
| RE43,527 E | 7/2012 | Popp |
| 8,491,839 B2 | 7/2013 | Popp |
| 8,591,811 B2 | 11/2013 | Popp |
| 8,660,680 B2 | 2/2014 | Popp |
| 9,008,815 B2 | 4/2015 | Popp |
| 9,092,028 B2 | 7/2015 | Popp |
| 9,195,228 B2 | 11/2015 | Popp |
| 9,304,509 B2 | 4/2016 | Popp |
| 2008/0282026 A1* | 11/2008 | Selker ............... A61L 2/0035 711/103 |
| 2011/0208436 A1* | 8/2011 | Page ................. G06Q 50/22 702/19 |
| 2016/0041551 A1 | 2/2016 | Popp |

OTHER PUBLICATIONS

Hiyama, Y., "Fiscal Year 2008 Study Report on Research on the Construction of Steady and Efficient Processes for the Manufacture, Development, and Approval Review of Drugs," Health and Labour Sciences Research Grant in Fiscal Year 2008 (Research on Regulatory Science of Pharmaceuticals and Medical Devices), 12 pages.

Hiyama, Y., et al., "Quality Overall Summary Mock P2 (Description Examples)," English Mock QOS P2_090406 MHLW Sponsored Science Research Study: Establishing Design Space in Critical Steps and Control Strategy, Mar. 2009, 59 pages.

"ICH Harmonised Tripartite Guideline: Pharmaceutical Development Q8(R2)," Current Step 4 Version, International Conference on Harmonisation of Technical Requirements for Registration of Pharmaceuticals for Human Use, Aug. 2009, 28 pages.

"Revision of the Guideline for Pharmaceutical Development," PFSB/ELD Notification 0628 No. 1, Director of Evaluation and Licensing Division (ELD), Pharmaceutical and Food Safety Bureau (PFSB), Ministry of Health, Labour and Welfare, <http://www.pmda.go.jp/ich/q/q8r2_10_6_28.pdf>, Jun. 28, 2010, 29 pages.

International Search Report and Written Opinion dated Sep. 11, 2012, issued in corresponding International Application No. PCT/JP20121067287, filed Jul. 6, 2012, 5 pages.

International Preliminary Report on Patentability, dated Jan. 14, 2014, issued in corresponding International Application No. PCT/JP2012/067287, filed Jul. 6, 2012, 5 pages.

Extended European Search Report dated Apr. 24, 2015, issued in corresponding European Application No. 12811023.6, filed Jul. 6, 2012, 8 pages.

Nasr, M.M., "Pharmaceutical Development: ICH Q8/Q(8)R," presentation at Workshop on Implementation of ICH Q8/Q9/Q10, Beijing, Dec. 3-5, 2008, 35 pages.

Peterson, J.J., "A Bayesian Approach to the ICH Q8 Definition of Design Space," Journal of Biopharmaceutical Statistics 18(5):959-975, 2008.

* cited by examiner

[Figure 1]
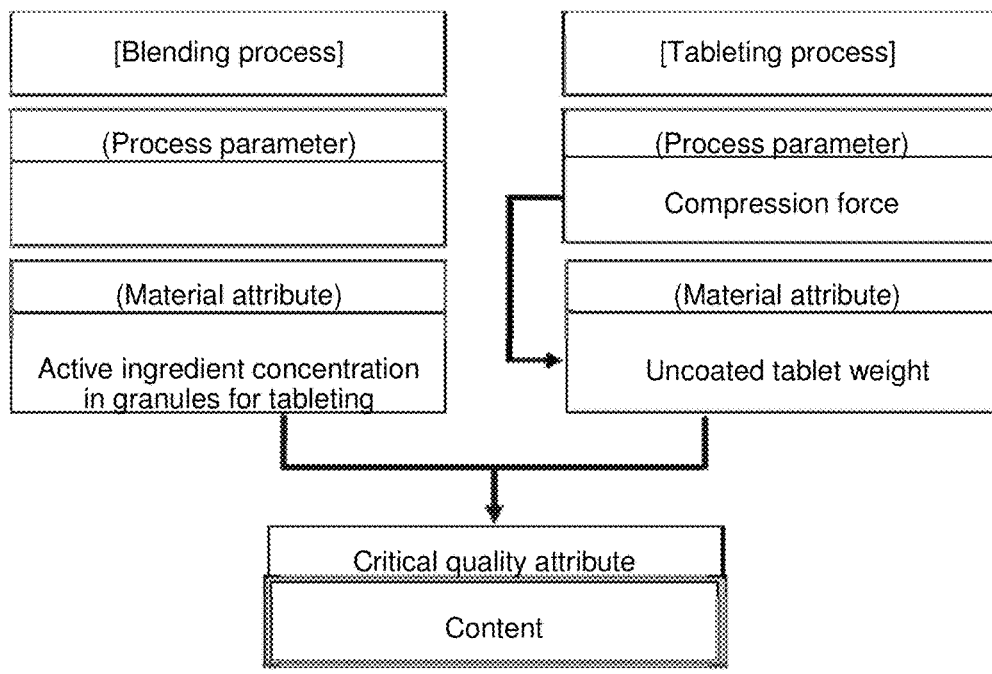

[Figure 2]
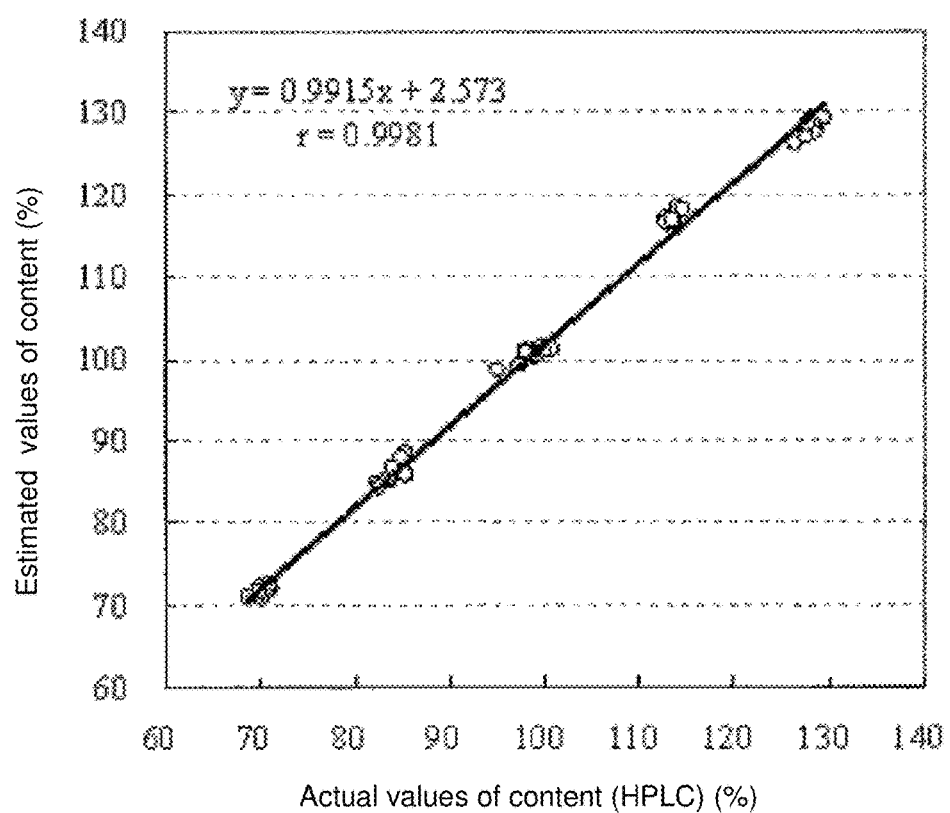

[Figure 3]
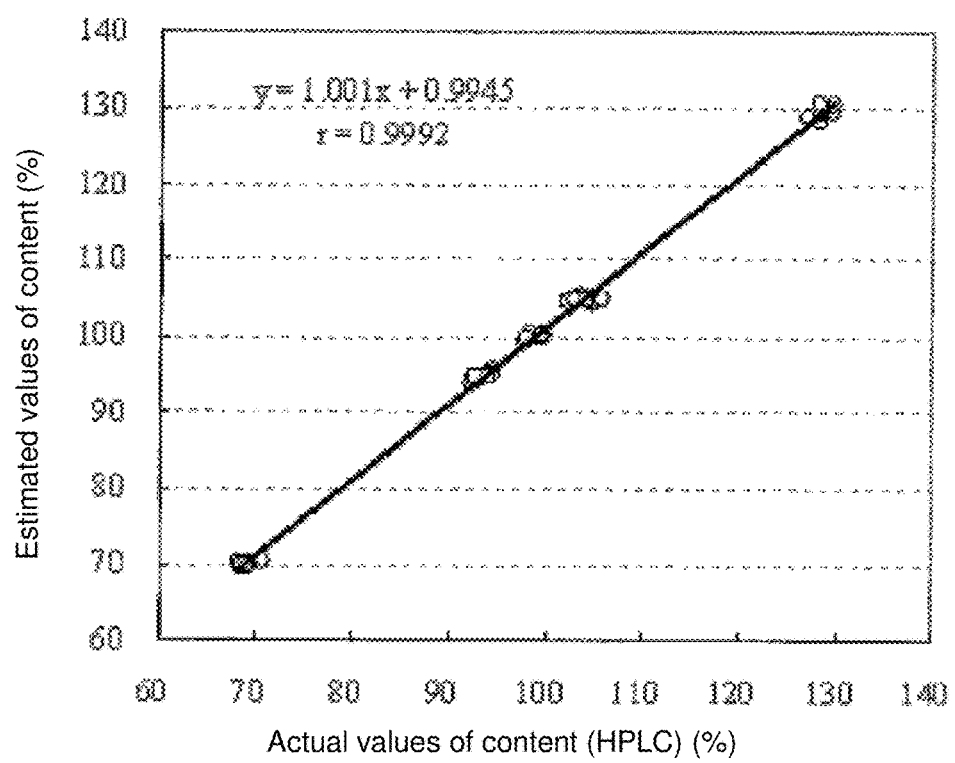

[Figure 4]
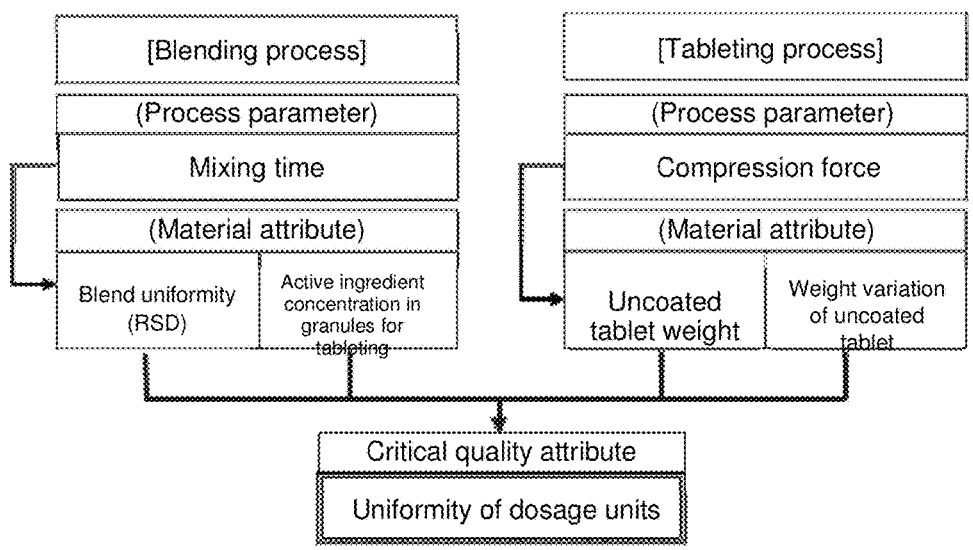

[Figure 5]
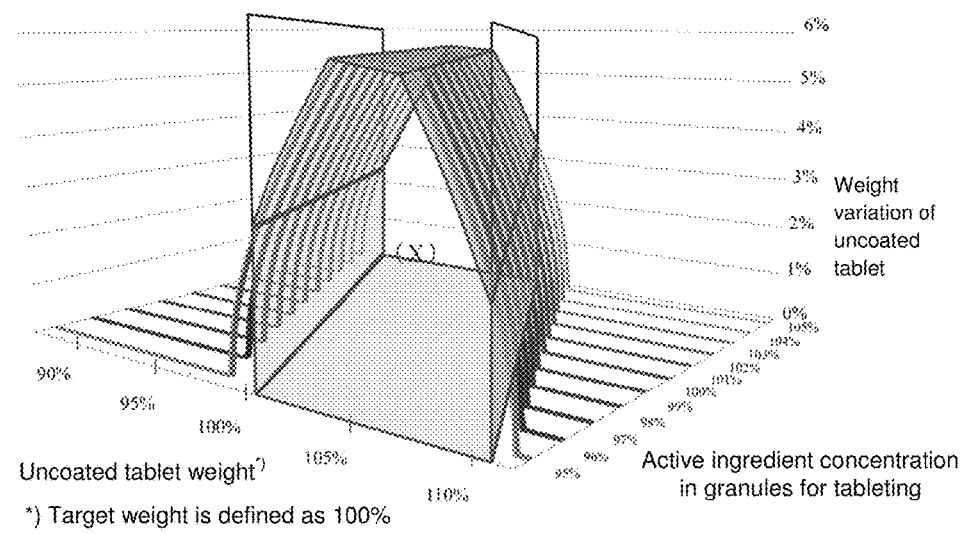
Uncoated tablet weight*)
*) Target weight is defined as 100%
[Figure 6a]
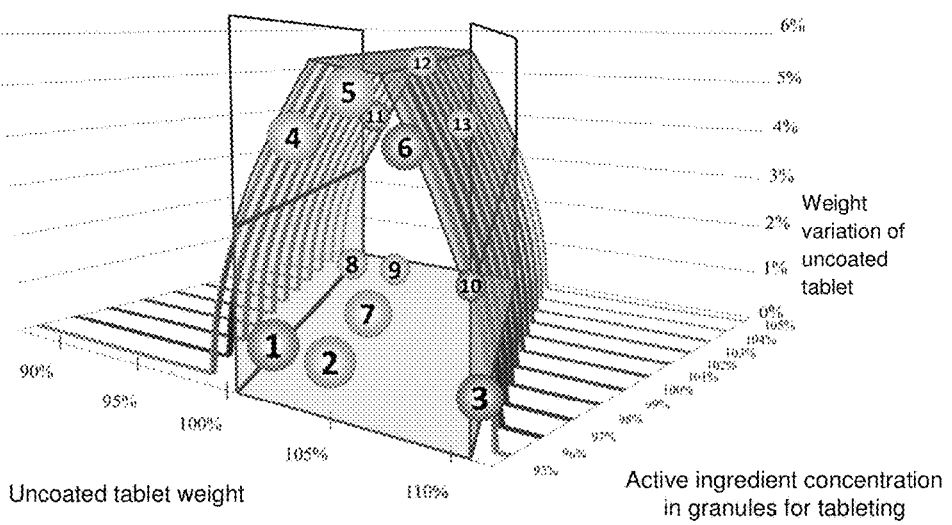
Uncoated tablet weight
All validation points 1 to 13 fall within conditions
that satisfy the uniformity of dosage units

[Figure 6b]
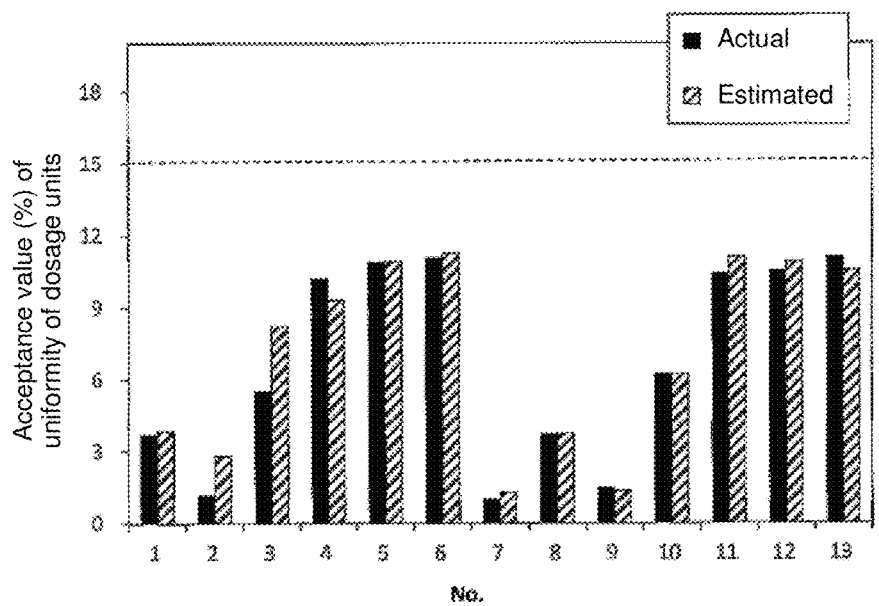
[Figure 6c]
| Validation point | Active ingredient concentration (%) in granules for tableting | Uncoated tablet weight (%) | Weight variation of uncoated tablet (%) |
|---|---|---|---|
| 1 | 96.9 | 100.5 | 0.3 |
| 2 | 96.9 | 102.7 | 0.4 |
| 3 | 96.9 | 110.2 | 0.3 |
| 4 | 96.9 | 100.2 | 3.8 |
| 5 | 96.9 | 105.0 | 5.3 |
| 6 | 96.9 | 108.3 | 3.8 |
| 7 | 100.6 | 100.4 | 0.3 |
| 8 | 103.9 | 92.7 | 0.5 |
| 9 | 103.9 | 96.9 | 0.3 |
| 10 | 103.9 | 102.4 | 0.2 |
| 11 | 103.9 | 92.0 | 3.9 |
| 12 | 103.9 | 96.0 | 5.2 |
| 13 | 103.9 | 100.0 | 3.8 |

[Figure 7]

| Factors that may influence drug product quality | |
|---|---|
| Manufacturing process | Factor |
| Drug substance | (metal) adhesion, flowability, crystal form, transfer, water content, cohesive properties, hygroscopic properties, solubility (degree of dissolution), melting point, physical stability (deliquescence, efflorescence, sublimability, etc.), chemical stability, particle shape, particle size (particle size distribution), pKa, residual solvents, wettability, specific surface area, and change in state (gelation, etc.) |
| Excipient | sedimentation properties, crystal form, transfer, water content, cohesive properties, hygroscopic properties, solubility, melting point, physical stability (deliquescence, efflorescence, sublimability, etc.), manufacturers (suppliers, sites, etc.), grade, source materials, purity of components contained therein, manufacturing methods, surface state, compatibility with bulks (adsorption, etc.), interaction among excipients, compression moldability, particle size, wettability, and surface area |
| Granulation | particle size distribution (particle size), mesh size (bag filters or perforated plates), scale, loading amount, manufacturing parameters (spraying rate, etc.), seasonal effects, binders (concentration, viscosity, and type), addition methods (order of loading), water content after drying, water content during granulation, surface state (wettability) of granules, chemical change caused by moisture absorption, thermal decomposition, particle shape, specific volume, particle size-basis content, flowability, control parameters (temperature and air volume control), strength of granules |
| Blending | manufacturing parameters, mixer shape (mixing mechanism), materials for machines, scale, loading amount, adhesion of granules, addition methods for components to be added (order of loading, the presence or absence of sieving, and mesh size during sieving), flowability, main drug concentration in granules for tableting, particle size, particle shape, blend uniformity, specific volume, spreadability (filling rate) of lubricants, and strength of granules |
| Tableting | feeder shape/mechanism, pestle shape, manufacturing parameters, supply systems, scale, materials, adhesion, hopper shape, control parameters (APCON), compression time, particle size of granules, dispersibility of lubricants in granules, chemical change caused by moisture absorption, decomposition attributed to rise in tableting machine temperature, content segregation, uncoated tablet weight, weight variation, disintegration properties, uncoated tablet hardness/tablet density/tablet thickness, elution properties of uncoated tablet, and the presence or absence of score lines/imprinting |
| Coating | chemical change caused by moisture absorption, thermal decomposition, tablet weight (coating film amount), hardness, disintegration properties, manufacturing parameters, control parameters (temperature and air volume control), coating agents (concentration, viscosity, and type), strength of coating films, type of spray guns, scale, coater shape (baffle shape), water content during coating, water content after drying, seasonal effects, the presence or absence of score lines/imprinting, and wear/cracking/chipping |

PRODUCT QUALITY CONTROL METHOD

TECHNICAL FIELD

The present invention relates to a method for constructing design space related to a critical quality attribute of a product by a quality-by-design approach, controlling a manufacturing process using the design space, and realizing real-time release testing to ensure the critical quality attribute without carrying out end-product testing, and a product obtained by this method.

BACKGROUND ART

With recent market globalization, the production sites of manufacturing industries have spread worldwide. In the pharmaceutical field, clinical development proceeds concurrently in a plurality of countries by the exploitation of global clinical trials. New drug application, approval, and marketing are now performed in almost the same timing around the world.

In the case of manufacturing the same product at a plurality of manufacturing sites, it is important to ensure constant product quality by setting specifications. Since medicinal products are controlled under strict specifications, an applicant must set specifications for each product to be approved and undergo review of the specifications for their appropriateness by regulatory authorities. In general, whether products comply with the approved specifications is assessed by end-product testing of the final products. Recently, a method based on real-time release testing using data obtained in the manufacturing process has been proposed as quality testing to assess approval or non-approval for the shipment of end products. Real-time release testing eliminates end-product testing of the final products and therefore permits immediate shipment after manufacture. Examples of descriptions of approval application forms relating to real-time release testing in pharmaceutical development have been published (Non-patent Literatures 1 to 4). Nonetheless, they have been applied in only a few cases of actual new drug application.

In the case of manufacturing the same product at a plurality of manufacturing sites, large differences in the quality of available raw materials, manufacturing scale, the type of manufacturing equipment, the skill of personnel in charge of manufacture, etc. must be taken into consideration. At each manufacturing site, process parameters such as manufacturing equipment parameters, temperature, and/or reaction time must be adjusted according to its equipment or environment in order to achieve the required specifications for the end-product.

CITATION LIST

Non-Patent Literature

Non-patent Literature 1: ICH Harmonised Tripartite Guideline, Pharmaceutical Development Q8 (R2), Current Step 4 version, August 2009

Non-patent Literature 2: Yukio Hiyama, 2008 Health and Labour Sciences Research Grants (Research on Regulatory Science of Pharmaceuticals and Medical Devices), Research on the rapid and efficient process construction of pharmaceutical manufacturing or development and approval review, 2008 Joint Research Report, Research on the establishment of design space in critical steps and real-time release as a control strategy, etc.

Non-patent Literature 3: Yukio Hiyama et al., MHLW Sponsored Science Research Study, Establishing Design Space in critical steps and Control Strategy, Quality Overall Summary Mock P2 (Description Examples), March 2009, 1-57

Non-patent Literature 4: Application Form for Sakura Tablet, Mock-Up for the Manufacture Method, Specifications, and Test Method Columns of Drug Product (Sample Description), Application Form for Sakura tablet_V2_01_0900310, Research on the construction of steady and efficient processes for the manufacture, development, and approval review of drugs, First Section Meeting, 1-13

SUMMARY OF INVENTION

Technical Problem

An object of the present invention is to provide a method for establishing design space for constantly ensuring quality and a method for quality testing of a product using the design space.

Solution to Problem

Specifically, the present invention relates to:

[1] a method for establishing design space for a quality attribute of an in-process product and/or an end product, comprising establishing the design space using only material attributes as inputs;

[2] the method according to [1], wherein the method comprises the steps of:

(1) extracting material attributes and/or process parameters that influence the quality attribute of the in-process product and/or the end product;

(2) converting the process parameters to material attributes, if process parameters are included in the extracted items; and (3) calculating the correlation between the material attributes obtained in steps (1) and (2) and the quality attribute and preparing the design space using the correlation;

[3] the method according to [1] or [2], wherein the method establishes design space for a quality attribute of a drug product;

[4] the method according to [3], wherein the drug product is a tablet or a capsule;

[5] the method according to [4], wherein the quality attribute is an active pharmaceutical ingredient concentration in the tablet or the capsule;

[6] the method according to [5], wherein the material attributes are the active pharmaceutical ingredient concentration in granules for tableting or encapsulation and the weight of the uncoated tablet or the capsule;

[7] the method according to [6], wherein the method establishes design space for the content of an active ingredient according to the following expression (a):

[Expression 1]

$$\text{Content (\%) of an active ingredient} = \frac{Xa \cdot Wa}{100} \quad (a)$$

$Xa$: Active ingredient concentration in granules for tableting or encapsulation (vs. theoretical concentration %)

$\overline{Wa}$: Weight of uncoated tablet or capsule (vs. theoretical weight %)

[8] the method according to [4], wherein the quality attribute is the uniformity of dosage units of the tablet or the capsule;

[9] the method according to [8], wherein the material attributes are the blend uniformity, the active pharmaceutical ingredient concentration in granules for tableting or encapsulation, the weight of the uncoated tablet or the capsule, and the weight variation of the uncoated tablet or the capsule;

[10] the method according to [9], wherein the method establishes design space for the uniformity of dosage units according to the following expression (e):

[Expression 2]

Acceptance value (%) for uniformity of dosage units = (e)

$$\left| M - \frac{\overline{Xa} \cdot \overline{Wa}}{100} \right| + k \sqrt{s_w^2 \left( \frac{\overline{Xa}}{100} \right)^2 + s_x^2 \cdot \left( \frac{\overline{Wa}}{100} \right)^2}$$

$$M: \begin{cases} 98.5\% & \left( \frac{\overline{Xa} \cdot \overline{Wa}}{100} < 98.5\% \right) \\ \frac{\overline{Xa} \cdot \overline{Wa}}{100} & \left( 98.5\% \leq \frac{\overline{Xa} \cdot \overline{Wa}}{100} \leq 101.5\% \right) \\ 101.5\% & \left( 101.5\% \leq \frac{\overline{Xa} \cdot \overline{Wa}}{100} \right) \end{cases}$$

$\overline{Xa}$: Active pharmaceutical ingredient concentration in granules for tableting or encapsulation (vs. theoretical concentration %)

$\overline{Wa}$: Weight of uncoated tablet or capsule (vs. theoretical weight %)

k: 2.0 (when the number of samples is 30) or 2.4 (when the number of samples is 10)

$s_x$: Blend uniformity (Relative standard deviation %)

$s_w$: Weight variation of uncoated tablet or capsule (Relative standard deviation %)

[11] a method for quality testing of an in-process product and/or an end product, comprising using design space established using a method according to any one of [1] to [10];

[12] the method according to [11], wherein the method comprises the step of determining material attributes in the manufacturing process of the in-process product and/or the end product and assessing the quality of the in-process product and/or the end product from the determined values and the design space;

[13] an in-process product and/or an end product whose quality has been tested by a method according to [11] or [12];

[14] a drug product whose quality has been tested by a method according to [11] or [12];

[15] the method according to [11], wherein the method is used in real-time release testing of the end product;

[16] a system for quality testing of an in-process product and/or an end product, comprising a unit which assesses whether or not material attributes determined in a manufacturing process fall within the design space established using a method according to any one of [1] to [10];

[17] a method for establishing design space of an end product, comprising establishing the design space of the end product using the design space of two or more in-process products; and

[18] a method for establishing design space of an end product, comprising establishing the design space of the end product using the design space of two or more in-process products established by a method according to any one of [1] to [10].

Advantageous Effects of Invention

The present invention provides a method for establishing design space for constantly controlling and/or ensuring a critical quality attribute of a product in a manner independent of process parameter variation ascribable to manufacturing site and/or manufacturing equipment differences, and a method for quality testing using the design space.

BRIEF DESCRIPTION OF DRAWINGS

FIG. 1 shows a control strategy for the content of compound Ia (which is defined in the Examples).

FIG. 2 shows the relationship between observed and estimated content values at varying active pharmaceutical ingredient concentrations in granules for tableting.

FIG. 3 shows the relationship between observed and estimated content values at varying uncoated tablet weights.

FIG. 4 shows a control strategy for the uniformity of dosage units of compound Ia.

FIG. 5 shows design space constructed according to expressions (a) and (b), wherein the design space simultaneously satisfies a content of 95.0 to 105.0% and an acceptance value for uniformity of dosage units of 15.0% or lower in the case of a blend uniformity (RSD) of 5.0%.

FIG. 6a In order to verify the validity of the design space established in FIG. 5, arbitrary validation points were selected (validation points 1 to 13 of FIG. 6a), and an observed value of uniformity of dosage units was compared with an estimated value of uniformity of dosage units at each validation point (FIG. 6b).

FIG. 6b In order to verify the validity of the design space established in FIG. 5, arbitrary validation points were selected (validation points 1 to 13 of FIG. 6a), and an observed value of uniformity of dosage units was compared with an estimated value of uniformity of dosage units at each validation point (FIG. 6b).

FIG. 6c shows a list of the active pharmaceutical ingredient concentration in granules for tableting, the weight of the uncoated tablet, and the weight variation of the uncoated tablet at each validation point.

FIG. 7 is a table listing factors that may influence drug product quality on the basis of each step of a manufacturing process.

DESCRIPTION OF EMBODIMENTS

The terms used in the present specification will be described.

"Design space" refers to the multidimensional combination and interaction of input variables (material attributes and process parameters) in a manufacturing process that have been demonstrated to provide assurance of quality.

"In-process product" refers to a product that is not an end product but is obtained in the course of manufacturing an end product required to ensure quality.

"End product" refers to a final or finished product required to ensure quality. Examples of end products include medicinal drug products that are approved by the Pharmaceutical Affairs Law.

"Inputs" refer to variables in a manufacturing process and specifically refer to material attributes and/or process parameters.

"Material attributes" refer to characteristics derived from materials in a manufacturing process or parameters that represent the characteristics. Examples of the material attributes in the manufacture of drug products include, but are not limited to, the physical properties of an active pharmaceutical ingredient, the physical properties of each excipient (e.g., a diluent, a binder, or a lubricant), the particle size of the active pharmaceutical ingredient, the water content of granules during a granulation process, the particle size or content by particle size of granules, the blend uniformity or the active pharmaceutical ingredient concentration in granules for tableting in a blending process, the weight of the uncoated tablet in a tableting process, the weight variation of the uncoated tablet, the uncoated tablet hardness, or the content variation in a tableting process, and the tablet water content or the coating film amount in a coating process.

"Process parameter" refers to a parameter related to manufacturing operations, such as various settings of manufacturing equipment, reaction temperature, or reaction time. Examples of process parameters in the manufacture of drug products include, but are not limited to, reaction temperature, reaction time, the number of revolutions of a hammer mill, mesh size, or feed rate in a bulk manufacturing process, inlet air temperature, spraying rate, spray air flow rate, or inlet air volume in a granulation process, blending time or rotational speed in a blending process, compression pressure or the number of revolutions of a turntable in a tableting process, and inlet air temperature, spraying rate, spray air flow rate, inlet air volume, or the number of revolutions of a pan in a coating process.

"Quality attribute" refers to a physical, chemical, biological, or microbiological property or characteristic that should be within an appropriate limit, range, or distribution to ensure the desired product quality. Of the quality attributes, a particularly important one is referred to as a "critical quality attribute."

The phrase "establishing the design space using only material attributes as inputs" means that the design space is prepared using only material attributes as inputs in calculating the correlation between the inputs and the quality attribute to establish the design space.

"Real-time release testing" refers to testing that is able to evaluate the quality of an in-process product and/or an end-product, by testing results of raw materials and/or data obtained in a manufacturing process without carrying out end-product testing, and ensuring that the quality is acceptable.

"Quality" refers to a characteristic required for a product to comply with the intended use of the product. Arbitrary qualities to be controlled may be selected from among a plurality of characteristics by a manufacturer. The quality of a medicinal drug product may be any characteristic selectable by those skilled in the art without particular limitations. Examples thereof include, but are not limited to, the purity of an active pharmaceutical ingredient, the content of the active ingredient, the amount of impurities, the uniformity of dosage units, the dissolution properties of a solid drug product, and the appearance of a drug product.

The phrase "assessing the quality" means examining whether or not data on each material attribute obtained in a manufacturing process falls within the design space, to judge the in-process product, the end product, and/or the drug product as having the ensured quality of interest if the data falls within the design space and/or to judge the in-process product, the end product, and/or the drug product as not having the ensured quality of interest if the data falls outside the design space.

"Control strategy" refers to a planned set of controls, derived from current product and manufacturing process understanding, that ensures manufacturing process performance and product quality.

"Drug product" refers to an orally or parenterally administrable medicinal drug product, which may be a solid drug product or a nonsolid drug product. Examples of "drug products" include, but are not limited to, tablets, granules, powders, capsules, solutions, and injections.

"Active ingredient" in a drug product refers to an ingredient that exhibits drug efficacy and may be used interchangeably with "main drug" in the present specification.

Next, embodiments of the present invention will be specifically described.

One embodiment of the present invention relates to a method for establishing design space for a quality attribute of an in-process product and/or an end product, comprising establishing the design space using only material attributes as inputs. This method comprises the following steps (1) to (3):

(1) extracting material attributes and/or process parameters that influence the quality attribute of the in-process product and/or the end product;

(2) converting the process parameters to material attributes, if process parameters are included in the extracted items; and (3) calculating the correlation between the material attributes obtained in steps (1) and (2) and the quality attribute and preparing the design space using the correlation.

Another embodiment of the present invention relates to a method for quality testing of an in-process product and/or an end product, comprising using the design space thus established. The present invention relates to a method for examining, confirming, verifying, and/or ensuring the quality of an in-process product and/or an end product, comprising assessing the quality using design space established with only material attributes as inputs and further relates to a product obtained by such a method. The method for quality testing of the present invention comprises the step of determining material attributes in the manufacturing process of a product whose quality is to be examined and assessing the quality of the in-process product and/or the end product from the determined values and the design space. The in-process product and/or the end product is judged as satisfying the quality of interest if the determined values fall within the design space. The in-process product and/or the end product is judged as not satisfying the quality of interest if the determined values fall outside the design space. Preferably, the method of the present invention can be used in real-time release testing of a final drug product.

In order to design a manufacturing process, what quality a product should have is usually predetermined, and the manufacturing method is selected so as to achieve the quality. A more systematic approach to the development of the manufacturing process design involves product or manufacturing process understanding as well as consideration given to methods for manufacturing process control or quality risk management.

Real-time release testing is not quality testing that is conducted after manufacture of a product whose quality is to be ensured. Rather, this method ensures the quality of a product to be obtained on the basis of preliminarily studied data on factors in the manufacturing process that influence the quality of the product. Use of real-time release testing eliminates the need for pre-shipment quality testing and therefore advantageously permits immediate shipment after manufacture. Real-time release testing may be performed using design space indicated by the multidimensional combination of inputs in a manufacturing process that have been demonstrated to provide assurance of quality. In real-time release testing using design space, a product to be obtained finally is judged as satisfying the target quality if the data obtained in a manufacturing process falls within the defined design space. In pharmaceutical development, the approval of a certain design space by regulatory authorities permits manufacturing process improvements, within the design space described in the certificate of approval, without further review (Non-patent Literature 1).

Examples of factors in a manufacturing process that may influence quality include two factors: process parameters (e.g., various settings of equipment, reaction temperature, and reaction time) and material attributes ascribable to the characteristics of materials. In the case of using design space in conventional real-time release testing, the design space is defined by a combination of process parameters or a combination of material attributes and process parameters. In such a case, even only small differences in manufacturing site, manufacturing equipment, or manufacturing scale inevitably require reconstruction of the design space according to need because each process parameter varies. In pharmaceutical development, a certain design space defined by process parameters, even if approved by regulatory authorities, needs to be redefined when a manufacturing site, a manufacturing scale, or the like is changed, for example, due to the replacement of manufacturing equipment or its parts associated with manufacturing equipment failure, etc., or change in the number of the products to be produced. This is because the authorized design space may no longer be the optimum design space for ensuring the quality of products that are obtained by manufacture following such changes. The design space thus changed may need to be further reviewed by regulatory authorities. Thus, real-time release using design space established by the conventional method embraces the contradiction of necessary design space redefining or further review by regulatory authorities associated with changes in manufacturing conditions such as manufacturing equipment or manufacturing site, due to the design space having been established using process parameters, in spite of the advantage that manufacturing process improvements within the approved design space described in the dossier are permitted without further review.

The present inventors have considered a process parameter-independent construction of design space more capable of constantly ensuring quality to be important. Thus, the present inventors have attempted to establish design space by cross-sectionally analyzing study results at all small, medium, and large scales, not by using study results only at an actual production scale, and consequently found that design space can be established using only material attributes. The design space thus established using only material attributes merely requires defining process parameters so as to satisfy material attributes, even if the manufacturing site, manufacturing equipment, or manufacturing scale, or the like is changed. This means that arbitrary process parameters that satisfy material attributes can be set because the quality attribute is ensured on the basis of the material attributes. In addition, material attributes in each process are multidimensionally controlled. Thus, results about material attributes determined in the process can be used to adjust target values of the material attributes in subsequent or later processes. This can minimize quality variability in routine production.

The inputs (material attributes or process parameters) that influence the quality attribute of an in-process product and/or an end product can be selected using an approach usually performed by those skilled in the art. For example, in real-time release testing of a drug product, inputs (material attributes or process parameters) that influence the quality attribute of the drug product are extracted as candidates on the basis of past experience or results of preliminary testing. Next, whether or not the variation of these candidate inputs influences the quality attribute of the drug product is confirmed by experiments (see e.g., Non-patent Literatures 1 to 4). The International Conference on Harmonisation of Technical Requirements for Registration of Pharmaceuticals for Human Use (ICH) has issued various guidelines as to pharmaceutical development: Non-patent Literature 4, QUALITY RISK MANAGEMENT Q9, 2005 (Non-patent Literature 5), and PHARMACEUTICAL QUALITY SYSTEM Q10, 2008 (Non-patent Literature 6). The inputs that influence the quality attribute of the in-process product and/or the end product can be selected by those skilled in the art using approaches, etc. shown in these guidelines. Although the specific procedures are not limited to those shown herein, a quality attribute of interest is extracted and selected on the basis of the quality target product profile (QTPP) in order to ensure the desired quality of a drug product. Inputs that influence the quality attribute of interest are extracted and subjected to risk assessment (e.g., risk identification, risk analysis, or risk evaluation) to extract candidate inputs. Subsequently, whether or not variation of the candidate inputs influences the drug product quality attribute of interest is confirmed by experiments.

Thereafter, the design space is established. If a process parameter is included in the factors that influence the quality, a material attribute that is directly influenced by the process parameter is selected instead of the process parameter. Once the material attributes are thus extracted, those skilled in the art can calculate the correlation between the material attributes and the quality attribute by an approach known in the art. The design space is unambiguously defined using the correlation. Specifically, those skilled in the art set a specification of the quality attribute and prepare design space on the basis of this specification and the calculated correlation.

Next, the material attributes in the manufacturing process are determined for the in-process product and/or the end product to be examined. The in-process product and/or the end product is judged as attaining the quality of interest if the determined values fall within the design space. The in-process product and/or the end product is judged as not satisfying the quality of interest if the determined values fall outside the design space.

Examples of factors that may influence the drug product quality include, but are not limited to, the factors listed in FIG. 7.

An alternative embodiment of the present invention relates to a system for quality testing equipped with a unit which carries out the method for quality testing of the present invention, or a system for quality control using the system for quality testing. The system of the present invention comprises, but is not limited to, for example, a unit which determines material attributes preselected for ensuring the quality of interest (e.g., high performance liquid chromatography (HPLC), ultraviolet visible absorption spectrophotometers, near infrared spectroscopy, Raman spectroscopy, moisture meters, precision balances, hardness meters, and specific surface area analyzers), a unit which assesses whether or not the determined material attributes fall within the design space established with only material attributes as inputs (e.g., a computer), and a unit which displays the assessment results (e.g., a computer screen).

A further alternative embodiment of the present invention relates to an in-process product and/or an end product whose quality has been ensured by the method and/or the system for quality testing of the present invention. The present invention also relates to a medicinal drug product whose quality has been ensured by the method and/or the system for quality testing of the present invention.

A further alternative embodiment of the present invention relates to a method for establishing design space of an end product (preferably, a drug product), comprising establishing the design space of the end product using the design space of two or more in-process products. Each drug product is a mixture composed of many components or ingredients. Such a product, albeit depending on its type, also requires multiple steps for its manufacturing method and needs to have high quality as to a number of items (e.g., the content of an active ingredient, the amount of impurities, dissolution properties, or nature) as a medicinal product. Thus, the establishment of design space and real-time release testing using this design space have previously been regarded as being very difficult to achieve for a drug product. The method of the present invention establishes design space for ensuring material attributes of in-process products according to need and further constructs the design space of the end product using the design space composed of the material attributes of the in-process products. In this method, the design space of the in-process products may be established using either material attributes or process parameters as inputs and is preferably established using only material attributes as inputs.

Next, the present invention will be described in detail with reference to the Examples. However, the present invention is not in any way limited to these Examples.

EXAMPLES

Tablets used in the Examples had formulations described in Table 1 and contained $N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide p-toluenesulfonate monohydrate represented by the following formula (Ia) (also referred to as compound Ia in the present specification):

[Formula 1]

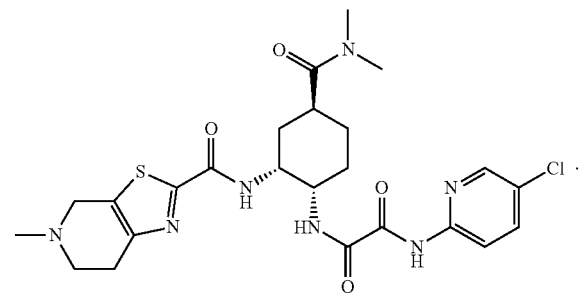

(Ia)

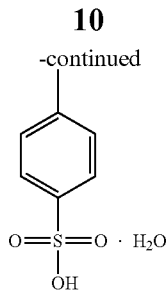

as an active ingredient. Compound Ia can be produced by a method described in, for example, WO2003/000657 or WO2003/000680 or a method equivalent thereto.

In order to prepare the tablets, components in the formulations described in Table 1 except for hydroxypropylcellulose and magnesium stearate were mixed and granulated with an aqueous solution of hydroxypropylcellulose. The resulting granules were mixed with magnesium stearate to prepare granules for tableting, which were then compressively molded into tablets. The uncoated tablets were coated by spraying with a coating solution obtained by dissolving a mixture of hypromellose, titanium oxide, talc, Macrogol 6000, and yellow ferric oxide or ferric oxide in purified water.

TABLE 1

| Formulation | 15 mg tablet (mg) | 30 mg tablet (mg) |
|---|---|---|
| Compound Ia | 20.2 | 40.4 |
| (in terms of compound I) | (15.0) | (30.0) |
| D-mannitol | q.s. | q.s. |
| Partially pregelatinized starch | 21 | 42 |
| Crospovidone | 5.4 | 10.7 |
| Hydroxypropylcellulose | 3.1 | 6.1 |
| Magnesium stearate | 0.8 | 1.6 |
| Total of uncoated tablet | 100 | 200 |
| Hypromellose | 3 | 6 |
| Titanium oxide | 0.3 | 0.6 |
| Talc | 1 | 2.1 |
| Macrogol 6000 | 0.6 | 1.2 |
| Yellow ferric oxide | trace | — |
| Ferric oxide | — | trace |
| Carnauba wax | trace | trace |
| Talc | trace | trace |
| Total of tablet | 105 | 210 |

Example 1

Active Ingredient Content of Final Drug Product (i. Method for Quality Assessment by Conventional Testing)

The 15 mg tablets were dissolved in a water/acetonitrile mixed solution (1:1). The amount of compound Ia was determined by HPLC. The amount of compound Ia was similarly calculated for the 30 mg tablets.

(ii. Method for Quality Assessment by Real-Time Release Testing)

Parameters in the manufacturing process that largely influenced the active ingredient content of the final drug products were studied in the light of findings gained over a plurality of manufacturing processes at 1-kg to 500-kg scales. As a result, the active ingredient concentration in granules for tableting in the blending process and the compression force and the weight of the uncoated tablet in the tableting process were identified as the parameters, as shown in FIG. 1. Although the final drug products were coated tablets, no manufacturing process parameters in the coating process were taken into consideration, because components that would affect the content of an active ingredient in an uncoated tablet are generally not used as coating agents. Thus, no manufacturing process parameter in the coating process was taken into consideration. Since the influence of the compression force, which is a process parameter, is reflected by the weight of the uncoated tablet, it was hypothesized that the active ingredient content of the final drug products could be controlled by the material attributes, i.e., the active ingredient concentration in granules for tableting in the blending process and the weight of the uncoated tablet in the tableting process. On the basis of this hypothesis, the following expression (a) using the concentration of compound Ia in the granules for compression and the weight of the uncoated tablet was set as the method for calculating an estimated content value:

[Expression 3]

$$\text{Content (\%) of an active ingredient} = \frac{\overline{Xa} \cdot \overline{Wa}}{100} \quad (a)$$

$\overline{Xa}$: Active ingredient concentration in granules for tableting or encapsulation (vs. theoretical concentration %)
$\overline{Wa}$: Weight of uncoated tablet or capsule (vs. theoretical weight %)

FIGS. 2 and 3 show results of evaluating the relationship between the actual value of the content of compound Ia and the value of the content of compound Ia estimated according to expression (a) in each tablet as regards the 30 mg tablets. The content of compound Ia in each tablet and the concentration of compound Ia in the granules for compression were determined by HPLC. FIG. 2 shows the relationship between the actual and estimated content values at varying active ingredient (main drug) concentrations in the granules for compression. FIG. 3 shows the relationship between the actual and estimated content values at varying uncoated tablet weights.

As shown in FIGS. 2 and 3, the correlation coefficient (the correlation coefficient is indicated by r in each diagram) between the actual value of the content of compound Ia and the value of the content of compound Ia estimated according to expression (a) in each tablet was 0.9981 or 0.9992, demonstrating that it was reasonable to calculate the active ingredient content according to expression (a).

Design space for the active ingredient content of the tablets containing compound Ia as an active ingredient was prepared by setting the value calculated according to expression (a) within an arbitrary range satisfying the quality required as a medicinal product. This design space was used in real-time release testing of the content to assess the quality.

Expression (a) described above depends only on the active ingredient concentration in granules for tableting and the weight of the uncoated tablet and as such, can be used in the establishment of design space for the active ingredient content of tablets without the need for taking into consideration material attributes (e.g., the degree of dissolution of the active ingredient) ascribable to the characteristics of the active ingredient and without limitation as to the type of active ingredient.

Example 2

Uniformity of Dosage Units of Final Drug Product (i. Method for Quality Assessment by Conventional Testing)

Testing on the uniformity of dosage units of tablets containing compound Ia is conducted according to content uniformity testing among the testing methods for uniformity of dosage units prescribed by the JP, US, and EP Pharmacopoeia. Specifically, the content of compound Ia in each drug product is determined by HPLC for ten or thirty 15 mg tablets. The acceptance value (AV) is calculated according to expression (b) shown below. The content is judged as being uniform among the drug products when the AV is 15.0% or lower (in the case of 10 samples) or 25.0% or lower (in the case of 30 samples). The content uniformity is assessed for the 30 mg tablets by similar calculation.

[Expression 4]

$$\text{Acceptance value } (AV)(\%) \text{ for content uniformity} = |M - \overline{X}| + ks \quad (b)$$

$\overline{X}$: Content (%) of an active ingredient in the drug product
$k$: 2.0 (when the number of samples is 30)
      or 2.4 (when the number of samples is 10)

$$M: \begin{cases} 98.5\% & (\overline{X} \leq 98.5\%) \\ \overline{X} & (98.5\% \leq \overline{X} \leq 101.5\%) \\ 101.5\% & (101.5\% \leq \overline{X}) \end{cases}$$

$$s: \text{Standard deviation} \sqrt{\frac{\sum_{i=1}^{n}(x_i - \overline{X})^2}{n-1}}$$

($n$ = the number of samples, $x_1, x_2, \ldots x_n$ each represent the active ingredient content of each individual sample tested)

(ii. Method for Quality Assessment by Real-Time Release Testing)

Parameters in the manufacturing process that largely influenced the uniformity of dosage units of tablets containing compound Ia as an active ingredient were studied in the light of findings gained over a plurality of manufacturing processes at 1-kg to 500-kg scales. As a result, the blending time, the blend uniformity, and the active ingredient concentration in granules for tableting in the blending process and the compression force, the weight of the uncoated tablet, and the weight variation of the uncoated tablet in the tableting process were extracted as the parameters, as shown in FIG. 4. Since the influence of the blending time and the compression force, which are process parameters, is reflected by the blend uniformity and the weight of the uncoated tablet, respectively, it was hypothesized that the uniformity of dosage units of the final drug products could be controlled by the blend uniformity, the active ingredient concentration in granules for tableting, the weight of the uncoated tablet, and the weight variation of the uncoated tablet.

Expression (b) described as a method for calculating the acceptance value (AV) in content uniformity testing among the testing methods for uniformity of dosage units prescribed by the JP, US, and EP Pharmacopoeia can be described by the following expression (c) in light of the results of Example 1(ii):

[Expression 5]

Acceptance value $(AV)(\%)$ for content uniformity= (c)

$$\left| M - \frac{\overline{Xa} \cdot \overline{Wa}}{100} \right| + ks$$

$$M: \begin{cases} 98.5\% & \left( \frac{\overline{Xa} \cdot \overline{Wa}}{100} \leq 98.5\% \right) \\ \frac{\overline{Xa} \cdot \overline{Wa}}{100} & \left( 98.5\% \leq \frac{\overline{Xa} \cdot \overline{Wa}}{100} \leq 101.5\% \right) \\ 101.5\% & \left( 101.5\% \leq \frac{\overline{Xa} \cdot \overline{Wa}}{100} \right) \end{cases}$$

$\overline{Xa}$: Active ingredient concentration in granules for tableting or encapsulation (vs. theoretical concentration %)
$\overline{Wa}$: Weight of uncoated tablet or capsule (vs. theoretical weight %)
k: 2.0 (when the number of samples is 30) or 2.4 (when the number of samples is 10)

The standard deviation s is calculated according to the following expression (d) using the active ingredient concentration in granules for tableting, the weight of the uncoated tablet, the blend uniformity, and the weight variation of the uncoated tablet (Chem. Pharm. Bull. 49 (11), 1412-1419 (2001)):

[Expression 6]

$$s = \sqrt{s_w^2 \cdot \left( \frac{\overline{Xa}}{100} \right)^2 + s_x^2 \cdot \left( \frac{\overline{Wa}}{100} \right)^2}$$  (d)

$s_x$: Blend uniformity (Relative standard deviation %)
$s_w$: Weight variation of uncoated tablet (Relative standard deviation %)
($\overline{Xa}$ and $\overline{Wa}$ are as defined above in expression (c))

On the basis of the hypothesis that the uniformity of dosage units could be controlled by the blend uniformity, the active ingredient concentration in granules for tableting, the weight of the uncoated tablet, and the weight variation of the uncoated tablet, the following expression (e) was set as the method for calculating the uniformity of dosage units:

[Expression 7]

Acceptance value (%) for uniformity of dosage units = (e)

$$\left| M - \frac{\overline{Xa} \cdot \overline{Wa}}{100} \right| + k \sqrt{ s_w^2 \cdot \left( \frac{\overline{Xa}}{100} \right)^2 + s_x^2 \cdot \left( \frac{\overline{Wa}}{100} \right)^2 }$$

($\overline{Xa}$, $\overline{Wa}$, $s_x$, $s_w$, M,
and k are as defined above in expressions (c) and (d))

The value calculated according to expression (e) using each parameter value obtained in the manufacturing process was almost the same as the value calculated according to expression (b), demonstrating that it was reasonable to calculate the uniformity of dosage units according to expression (e).

Design space for the uniformity of dosage units of the tablets containing compound Ia as an active ingredient was prepared by setting the acceptance value (%) for uniformity of dosage units calculated according to expression (e) within an arbitrary range satisfying the quality required as a medicinal product. This design space was used in real-time release testing of the uniformity of dosage units to assess the quality.

Expression (e) described above depends only on the blend uniformity, the active ingredient concentration in granules for tableting, the weight of the uncoated tablet, and the weight variation of the uncoated tablet and as such, can be used in the establishment of design space for the uniformity of dosage units of tablets without the need for taking into consideration material attributes (e.g., the degree of dissolution of the active ingredient) ascribable to the characteristics of the active ingredient and without limitation as to the type of active ingredient.

Example 3

Simultaneous Assessment of Active Ingredient Content and Uniformity of Dosage Units of Final Drug Product (i. Method for Quality Assessment by Conventional Testing)

The procedures of (i. Method for quality assessment by conventional testing) of (Example 1) and (i. Method for quality assessment by conventional testing) of (Example 2) are each carried out to respectively assess the specification compliance of the active ingredient content and the uniformity of dosage units of the final drug product.

(ii. Method for Quality Assessment by Real-Time Release Testing)

Design space for use in testing the specification compliance of the active ingredient content and the uniformity of dosage units of the drug product (tablets) containing compound Ia as an active ingredient was established using the results of Examples 1(ii) and 2(ii). This establishment employed four material attributes (the active ingredient concentration in granules for tableting, the weight of the uncoated tablet, the blend uniformity (RSD), and the weight variation of the uncoated tablet) shown in FIGS. 1 and 4. FIG. 5 shows design space (space (X) in the diagram) when the specifications for the active ingredient content and the uniformity of dosage units were set to 95.0 to 105.0% and 15.0%, respectively. The design space shown in FIG. 5 is based on a blend uniformity (RSD) of 5.0%.

The material attributes (the active ingredient concentration of granules for tableting, the weight of the uncoated tablet, and the weight variation of the uncoated tablet) of the final drug product were assessed for their compliance with the design space. As a result, the specification compliance of the active ingredient content and the uniformity of dosage units of the final drug product was successfully assessed simultaneously.

(iii. Verification of Validity of Established Design Space)

In order to verify the validity of the design space established in the preceding paragraph ii, arbitrary validation points were selected (validation points 1 to 13 of FIG. 6a). FIG. 6c shows a list of the active ingredient (main drug) concentration in granules for tableting, the weight of the uncoated tablet, and the weight variation of the uncoated tablet at each validation point. All of these validation points fall within the scope of expression (e) in the case of an acceptance value of uniformity of dosage units of 15.0%. The actual value for uniformity of dosage units was compared with the estimated value of uniformity of dosage units at each validation point. As a result, no large difference was found between the observed values of uniformity of dosage units and the estimated values of uniformity of dosage units at all the validation points (FIG. 6b).

INDUSTRIAL APPLICABILITY

The present invention provides a process parameter-independent method for quality control of a product using design space and further provides a method for quality testing of a product using real-time release testing. The method of the present invention enables easy continuation of manufacture of products of the same quality even when the manufacturing site, manufacturing equipment, or manufacturing scale is changed.

The invention claimed is:

1. A method for real-time release testing of a product in a manufacturing process for a quality attribute, comprising:
    (a) establishing a design space for the quality attribute of the product using only material attributes as inputs, wherein establishing the design space comprises the steps of:
        (1) extracting one or more first material attributes of one or more materials used in the manufacturing process and one or more manufacturing process parameters used in the manufacturing process that influence the quality attribute of the product;
        (2) converting the one or more manufacturing process parameters to one or more second material attributes, wherein the one or more second material attributes are directly influenced by the one or more manufacturing process parameters;
        (3) calculating a correlation between the one or more first material attributes and the one or more second material attributes and the quality attribute; and
        (4) preparing the design space using the correlation and setting a value of a calculated quality attribute to within a range of acceptable values;
    (b) performing the manufacturing process according to the design space;
    (c) determining the one or more first material attributes and the one or more second material attributes in the manufacturing process; and
    (d) assessing the quality attribute of the product from the determined one or more first material attributes and one or more second material attributes and the design space to provide a quality attribute test result.

2. The method according to claim 1, wherein the method establishes design space for a quality attribute of a drug product.

3. The method according to claim 2, wherein the drug product is a tablet or a capsule.

4. The method according to claim 3, wherein the quality attribute is the content of an active ingredient in the tablet or the capsule.

5. The method according to claim 4, wherein the material attributes are the active ingredient concentration in granules for tableting or encapsulation and the weight of the uncoated tablet or the capsule.

6. The method according to claim 5, wherein the method establishes design space for the content of an active ingredient according to the following expression (a):

$$\text{Content (\%) of an active ingredient} = \frac{\overline{Xa} \cdot \overline{Wa}}{100} \quad (a)$$

wherein $\overline{Xa}$: Active ingredient concentration in granules for tableting or encapsulation (vs. theoretical concentration %), and $\overline{Wa}$: Weight of uncoated tablet or capsule (vs. theoretical weight %).

7. The method according to claim 3, wherein the quality attribute is the uniformity of dosage units of the tablet or the capsule.

8. The method according to claim 7, wherein the material attributes are the blend uniformity, the active ingredient concentration in granules for tableting or encapsulation, the weight of the uncoated tablet or the capsule, and the weight variation of the uncoated tablet or the capsule.

9. The method according to claim 8, wherein the method establishes design space for the uniformity of dosage units according to the following mathematical expression (e):

$$\text{Acceptance value (\%) for uniformity of dosage units} = \quad (e)$$

$$\left| M - \frac{\overline{Xa} \cdot \overline{Wa}}{100} \right| + k \sqrt{s_w^2 \cdot \left(\frac{\overline{Xa}}{100}\right)^2 + s_x^2 \cdot \left(\frac{\overline{Wa}}{100}\right)^2}$$

$$M: \begin{cases} 98.5\% & \left(\frac{\overline{Xa} \cdot \overline{Wa}}{100} \leq 98.5\%\right) \\ \frac{\overline{Xa} \cdot \overline{Wa}}{100} & \left(98.5\% \leq \frac{\overline{Xa} \cdot \overline{Wa}}{100} \leq 101.5\%\right) \\ 101.5\% & \left(101.5\% \leq \frac{\overline{Xa} \cdot \overline{Wa}}{100}\right) \end{cases}$$

wherein $\overline{Xa}$: Active ingredient concentration in granules for tableting or encapsulation (vs. theoretical concentration %), $\overline{Wa}$: Weight of uncoated tablet or capsule (vs. theoretical weight %), k: 2.0 (when the number of samples is 30) or 2.4 (when the number of samples is 10), $s_x$: Blend uniformity (Relative standard deviation %), and $s_w$: Weight variation of uncoated tablet or capsule (Relative standard deviation %).

10. The method according to claim 1, wherein the method is used in real-time release testing of an end product.

11. The method according to claim 1, wherein the design space of an end product is established using the design space of two or more in-process products.

12. The method of claim 1, further comprising performing experiments to confirm that the one or more first material attributes of one or more materials used in the manufacturing process and the one or more manufacturing process parameters used in the manufacturing process influence the quality attribute.

13. The method of claim 1, wherein determining the one or more first material attributes includes measuring a physical property of the one or more materials used in the manufacturing process; and wherein determining the one or more second material attributes of the product includes measuring a physical property of the product.

* * * * *